(12) United States Patent
Masakov et al.

(10) Patent No.: US 7,367,950 B1
(45) Date of Patent: May 6, 2008

(54) DISTRIBUTED APPARATUS AND METHOD FOR NON-INVASIVE MEASUREMENT OF FUNCTIONAL STATE AND ADAPTIVE RESPONSE

(75) Inventors: Leonid Vasilyevich Masakov, Eugene, OR (US); Vladimir Borisovich Larionov, Eugene, OR (US)

(73) Assignee: Omegawave, LLC, Portland, OR (US)

( * ) Notice: Subject to any disclaimer, the term of this patent is extended or adjusted under 35 U.S.C. 154(b) by 69 days.

(21) Appl. No.: 11/386,974

(22) Filed: Mar. 21, 2006

Related U.S. Application Data (63) Continuation-in-part of application No. 10/452,609, filed on May 30, 2003, now abandoned, which is a continuation of application No. 09/854,988, filed on May 13, 2001, now Pat. No. 6,572,558.

(60) Provisional application No. 60/204,424, filed on May 13, 2000.

(51) Int. Cl.
*A61B 5/02* (2006.01)
*A61B 5/04* (2006.01)
*A61B 5/00* (2006.01)

(52) U.S. Cl. .................. 600/483; 600/300; 600/481; 600/513; 600/509; 600/544; 128/920

(58) Field of Classification Search ............... 600/481, 600/483, 300, 301, 500–504, 508–526, 544, 600/545, 552–559
See application file for complete search history.

(56) References Cited

U.S. PATENT DOCUMENTS

| | | | | |
|---|---|---|---|---|
| 5,596,994 | A * | 1/1997 | Bro | 600/545 |
| 5,771,897 | A * | 6/1998 | Zufrin | 600/483 |
| 5,941,820 | A * | 8/1999 | Zimmerman | 600/300 |
| 6,052,619 | A * | 4/2000 | John | 600/544 |
| 6,234,964 | B1 * | 5/2001 | Iliff | 600/300 |
| 6,493,577 | B1 * | 12/2002 | Williams | 600/544 |
| 6,572,558 | B2 * | 6/2003 | Masakov et al. | 600/483 |

* cited by examiner

*Primary Examiner*—Charles A. Marmor, II
*Assistant Examiner*—Navin Natnithithadha
(74) *Attorney, Agent, or Firm*—Steven J. Adamson (57) ABSTRACT

An apparatus and method for distributed, non-invasive assessment of the functional state and state of adaptive response of a subject under test. The functional state tests may include heart rate variability, differential ECG, omega brain wave, jump and stimulus response tests. A plurality of data collection (and result display) units are provided, and collected data is propagated over the internet or another network to a centralized processing computer that performs the functional state assessments and returns the results.

17 Claims, 7 Drawing Sheets

| PARAMETER | VALUE | NORM | CURRENT FUNCTIONAL STATE OF ENERGY SUPPLY SYSTEM IS CHARACTERIZED BY: |
|---|---|---|---|
| AEROBIC POWER INDEX | 67 | 58-95 | SATISFACTORY FUNCTIONAL RESERVE; |
| AEROBIC EFFICIENCY INDEX | 70 | 60-90 | |
| ALACTATIAL QUANTITY INDEX | 15 | 11-25 | DECREASING OF THE SPEED OF THE RECOVERY PROCESSES; |
| LACTATIAL QUANTITY INDEX | 15 | 12-20 | |
| ANAEROBIC POWER INDEX | 103 | 100-300 | MODERATE RESISTANCE TO HYPOXIA; |
| MAIN METHABOLIC POWER INDEX | 214 | 210-250 | |
| SYSTEM'S ADAPTION INDEX | 134 | 120-148 | GOOD AEROBIC RESERVES |
| HR AT MAXIMUM OXYGEN CONSUMPTION | 188 | 179-210 | |
| HR AT ANAEROBIC LEVEL | 169 | 150-180 | |

Fig. 11

| CHANGE OF THE Ω POTENTIAL AFTER A LOAD IN % OF THE BASE POTENTIAL | CHARACTERISTICS OF THE MECHANISMS OF REGULATION OF SYSTEMS (CORRESPONDING TO TIME ZONES) | | |
|---|---|---|---|
| | A | B | C |
| >25 | INSIGNIFICANT HYPERFUNCTION | SIGNIFICANT HYPERFUNCTION | INSIGNIFICANT HYPERFUNCTION |
| >50 | SIGNIFICANT HYPERFUNCTION | SIGNIFICANT HYPERFUNCTION | SIGNIFICANT HYPERFUNCTION |
| FROM 0 TO ±25 | NORM | INSIGNIFICANT HYPERFUNCTION | NORM |
| <25 | INSIGNIFICANT HYPOFUNCTION | NORM | INSIGNIFICANT HYPOFUNCTION |
| <50 | SIGNIFICANT HYPOFUNCTION | NORM | SIGNIFICANT HYPOFUNCTION |

Fig. 14

BEGIN → INITIAL CLASSIFICATION, CONCLUSION → REFINED CLASSIFICATION, CONCLUSION → END

DISTRIBUTED APPARATUS AND METHOD FOR NON-INVASIVE MEASUREMENT OF FUNCTIONAL STATE AND ADAPTIVE RESPONSE

CROSS REFERENCE TO RELATED APPLICATIONS

This application is a continuation-in-part of U.S. patent application Ser. No. 10/452,609, filed May 30, 2003 now abandoned, and entitled Apparatus And Method For Non-Invasive Measurement Of Current Functional State And Adaptive Response In Humans, which is a continuation of U.S. patent application Ser. No. 09/854,988, filed on May 13, 2001, and now issued as U.S. Pat. No. 6,572,558. Application Ser. No. 09/854,988 claims the benefit of earlier filed U.S. provisional patent application, No. 60/204,424, filed May 13, 2000, by the inventors listed above and entitled Apparatus and Method for Diagnosing Physical State and Potential.

FIELD OF THE INVENTION

The present invention relates to distributed, non-invasive assessment of the current functional state and/or adaptive response to stress of a human or animal under test.

BACKGROUND OF THE INVENTION

The human body is constantly being stressed (*The Stress of Life*, Hans Selye, Md., McGraw Hill, rev. ed., (1978)). Positive adaptation to stress can lead to an improved physical state (e.g., athletic training), while a breakdown in adaptation can result in the onset of significant medical conditions (e.g., heart attack, etc.).

Monitoring changes in a person's functional state and state of homeostasis provides an understanding of that person's adaptation to stress. In order to see changes in a person's functional state and state of homeostasis, testing must be done on a frequent basis and must include test of the major systems in the human body. These include the systems that regulate cardiac activity, energy metabolism, the central nervous system, the gas exchange and cardio-pulmonary (circulatory) system, the detoxification system and the hormonal (adrenal) system.

Various invasive and non-invasive tests are known for assessing the functional state of a person. Invasive tests include blood tests and biopsies, etc., that damage tissue in carrying out the test. Disadvantages of invasive tests include pain, tissue damage, risk of infection and inability to perform the test with high frequency (due to the associated tissue damage). Invasive tests also tend to be relatively expensive and often require a visit to a medical facility (as opposed to home or field use).

Pseudo-invasive tests include tests that are not literally invasive, but which cannot be repeated with high regularity due to deleterious effects on the body. Examples include X-rays (excess radiation) and VO2 maximum treadmill tests which require a person to run to exhaustion (this may be difficult or impossible for person in a weakened physical state to perform regularly). With the exception of direct tissue damage, pseudo-invasive tests tend to suffer from the same disadvantages listed above for invasive tests.

Non-invasive tests tend to have much lower incidence of tissue damage or the like and, therefore, they can be practiced with higher frequency. Examples include temperature and blood pressure testing. While non-invasive tests are beneficial in that they can be practiced more regularly and tend to be less expensive, they are also disadvantageous in that they tend to provide a limited, direct measurement of a physical condition parameter. For example, a blood pressure reading simply states the current blood pressure, but does not provide information on what body system or systems are functioning improperly and causing the blood pressure to be high or low.

In order to better assess a person's health and adaptive response, it is desirable and part of the present invention to obtain and generate more information about that person's current functional state. This can be done in part by making indirect assessment of a person's health based on directly measured parameters. It can also be done by testing a greater number of body systems and/or strategically selecting or designing tests that provide comprehensive assessment data from a small number of tests.

A need thus exists for an apparatus and a method that provide a combination of non-invasive tests that more comprehensively, efficiently and inexpensively assess a person's current functional state and their state of adaptive response.

The art of physical and functional state assessment is also limited in that the equipment required for certain test, for example, cardiac and brainwave analysis, tends to be expensive and stand alone, requiring a "subject under test" (SUT) to travel regularly (and at great distances in rural areas) to the site of the machine for testing. This also necessitates a greater number of machines, one at each hospital or assessment facility, which in turn results in a greater overall expense for machines purchasing, increased cost per test to recuperate the purchasing cost and increased insurance rates, etc.

Thus, a need also exists for a distributed testing arrangement that permits SUTs to be tested where they are (eliminating unwanted travel and energy use) and drives down the overall cost of assessment and assessment equipment, among other advantageous.

SUMMARY OF THE INVENTION

Accordingly, it is an object of the present invention to provide comprehensive, efficient and inexpensive assessment of a person's or animal's current functional state and state of adaptive response.

It is another object of the present invention to provide this assessment in a non-invasive manner.

It is also an object of the present invention to provide a distributed assessment arrangement permitting local testing in a cost-effective manner.

These and related objects of the present invention are achieved by use of a distributed apparatus and method of non-invasive measurement of functional state and adaptive response as described herein.

In one embodiment, the present invention may include a plurality of data collection units each including a user interface and a processing logic, the data collection processing logic permitting a user to request one or more functional state test from the group of test including: heart rate variability test, differential ECG test, brain wave test, jump test, and stimulus response test; and a processing server configured for location at a distance from each of the data collection units and couplable through a network connection to the data collection units. The processing server that receives test requests and corresponding collected data from a data collection unit and performs the one or more requested tests to produce a signal for a given test that is representative of a textual conclusion of the functional state of a body system that that test is designed to assess.

Various other embodiments and arrangements, including method embodiments are also within the present invention as discussed herein.

The attainment of the foregoing and related advantages and features of the invention should be more readily apparent to those skilled in the art, after review of the following more detailed description of the invention taken together with the drawings.

DETAILED DESCRIPTION

The present invention is applicable to humans and to other animals. It is particularly well suited for animals involved in athletic competition such as race horses, dogs, camels, etc. The text that follows immediately below discusses functionality with respect to humans. It should be recognized that these teachings may also be extended to other animals without departing from the present invention. U.S. patent application Ser. No. 11/359,725, filed Feb. 21, 2006, for an Apparatus and Method for Non-Invasive Measurement of Current Functional State and Adaptive Response in Non Human Mammals by the same inventor as herein discusses non-invasive assessment of non-human mammals and is hereby incorporated by reference.

Homeostasis is the tendency to maintain internal stability within an organism by coordinated responses of the organ systems that automatically compensate for external stresses. In the human body, the major organ or body systems include cardiac, metabolic, circulatory, detoxification, hormonal (adrenal), central nervous (CN) and neuromuscular systems. The present invention provides for a plurality of tests that monitor the organ or body systems. Tests within the present invention include, but are not limited to, heart rate variability (HRV), differential ECG (DECG) and omega brain wave (OW). They may also include jump and stimulus response (SR) tests. The present invention assists in identifying which body systems are not functioning properly, i.e., affecting homeostasis, and how the body may be responding to a particular stress, e.g., exercise, dieting, illness, heart attach recovery, etc.

Figure 1:
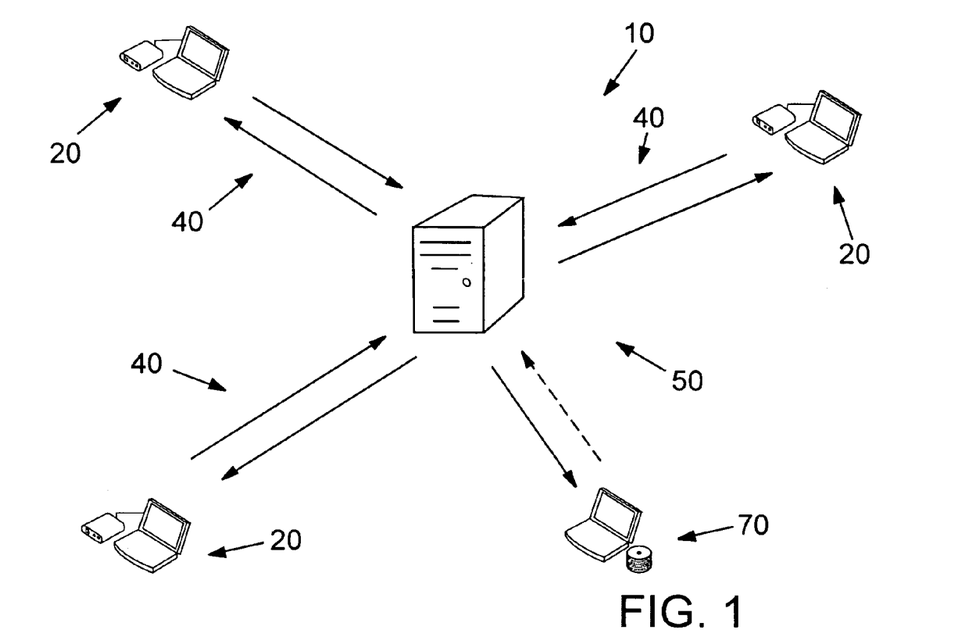
FIG. 1 is a diagrammatic representation of a distributed non-invasive testing system in accordance with the present invention.
Figure 2:
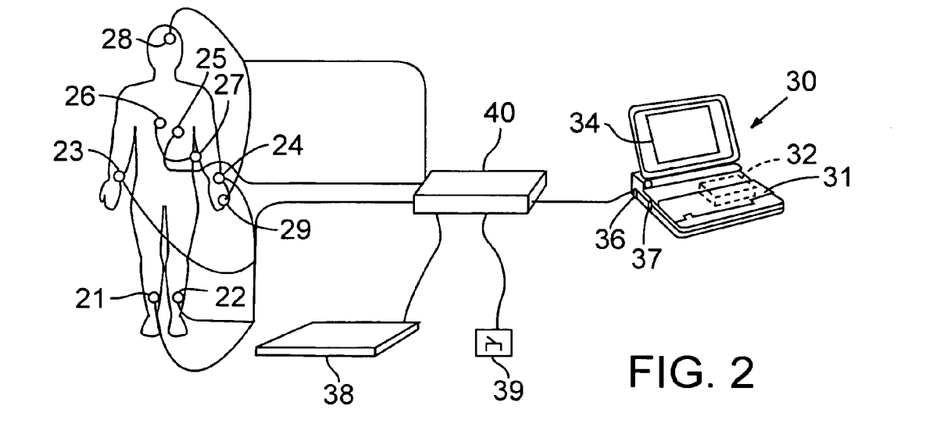
FIG. 2 is a perspective view of a data collection unit for the system of FIG. 1 in accordance with the present invention.

Referring to FIG. 1, a diagrammatic representation of embodiment of a distributed assessment system in accordance with the present invention is shown. This system 10 includes a plurality of remote data collection units (DCU) 20 which communicate via the internet or other wired or wireless network 45 with a data processing server 50. The server 50 analyses and processes data sent by each DCU, generates test results and returns them to the DCU from which they may be viewed by the "subject under test" SUT or a professional conducting the assessment. Referring to FIG. 2, a diagram of one embodiment of DCU 20 in accordance with the present invention is shown. FIG. 2 illustrates one arrangement, among others, of electrode/sensor placements on a human body.

Table I below provides a list of physical tests preferably conducted by the equipment of FIG. 1 and the corresponding body systems that are monitored by those tests.

TABLE I

| Body System Tests | |
|---|---|
| Tests | Body System Examined |
| 1. Heart Rate Variability | Cardio System |
| 2. Differential ECG | Metabolic |
| 3. Omega Wave | Circulation, Detox, Adrenal, CN |
| 4. Jump | Neuro-Muscular |
| 5. Stimulus Response | CN |

These five tests are preferred because they provide a relatively comprehensive assessment of functional state, by virtue of the various body systems that they measure/monitor. It should be recognized, however, that individual tests or combinations of tests (less than all), particularly when assessing a specific condition or response, may be performed as an alternative to conducting all tests. Furthermore, the HRV, DECG and omega wave tests are a preferred subset of tests because of the comprehensive and efficient assessment they afford. It should also be recognized that additional tests may be performed, e.g., a convention ECG, etc., and that the non-invasive tests taught herein may be used with or without invasive tests to determine the functional state of a person.

Each DCU 20 preferably includes a plurality of sensors 21-29 for assessing the functional state of a SUT 15. These include HRV sensors 21-24, additional DECG sensors 25-27 and omega wave sensors 28-29. Jump test sensors 38 and time response sensors 39, among others, may also be provided. These sensors are coupled to an interface device (ID) 40 that functions to channel signals through to a processing unit or computer 30 and to protect a SUT from electrical shock. ID 40 preferably amplifies, filters and digitizes analog signals from the sensors and propagates them to processor 30 when requested by same.

Computer 30 preferably includes a user interface that may have a keyboard 31, processing logic 32, monitor 34, wired connection ports 36 and an antenna 37 for wireless communication. It may be a laptop computer another mobile electronic device, a specially programmed PDA or other suitable device.

In use, a SUT is connected to the appropriate sensors and an operator at computer 30 selects the desired test or tests. Logic 32 responds by enabling receipt of sensor input from the respective sensors for the requisite time interval. This information is then bundled and sent via the internet 45 to server 50.

Server 50 may be any suitable computing device that is capable of carrying out the functionality described herein. Many "server" type computers are known in the art.

Figures 3, 4:
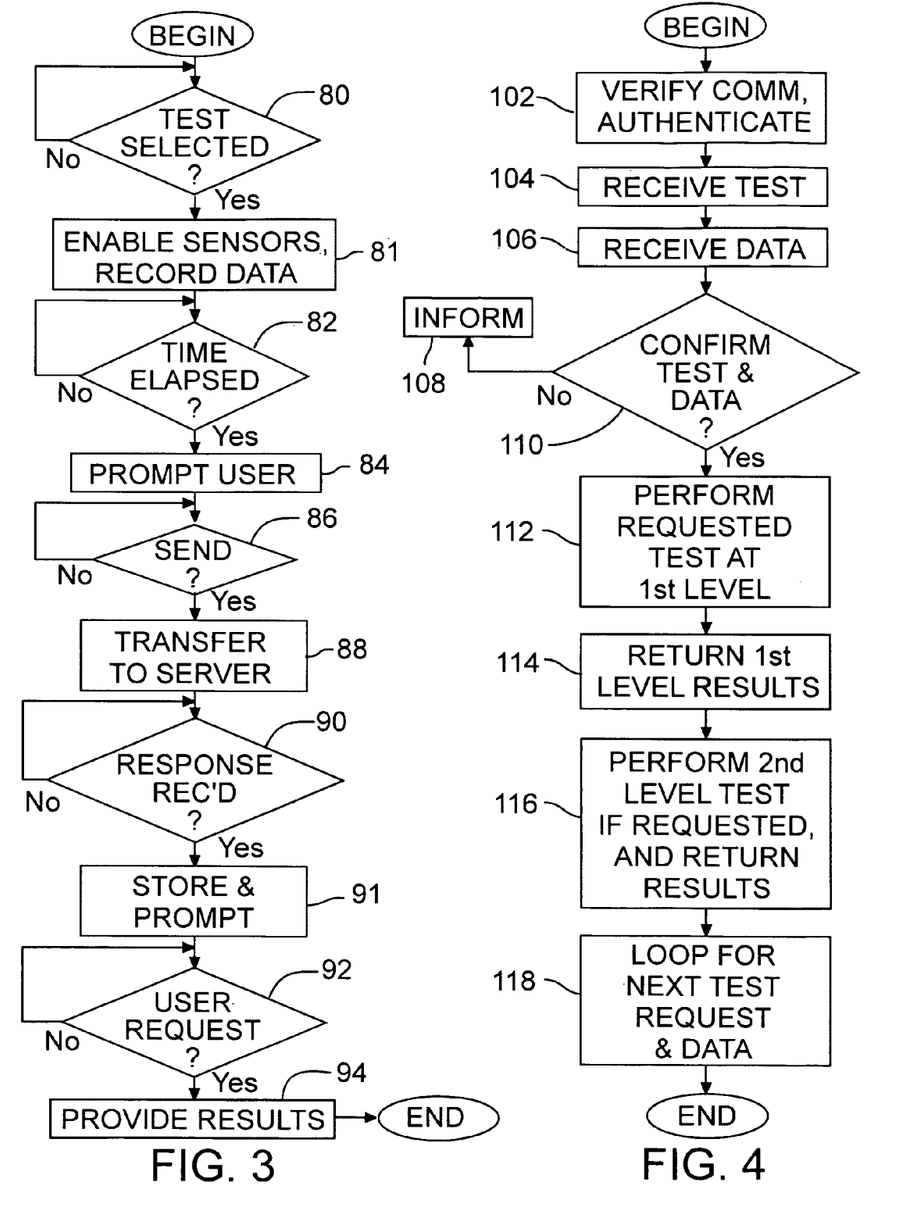
FIG. 3 is a flow diagram of processing within the data collection unit of FIG. 2.
FIG. 4 is a flow diagram of processing in a server or processing computer for the system of FIG. 1.

Referring to FIG. 3, a flow diagram of processing within a DCU in accordance with the present invention is shown. When invoked, processing logic operating in computer 30 awaits selection of a desired test or tests (step 80). Through an onscreen selection or other known means, the user may select among cardiac (HRV), energy system (DECG), Omega Wave, speed/power (jump) and sensory (reaction) assessments. One, some or all tests can be selected. The first three do not require action by the user. For those, the appropriate electrodes/sensors are connected and the interface device 31 is enabled to receive and propagate sensed data to computer 30 (step 81). Data is collected for the requisite time period and stored in computer 30 (step 82). A user may then be prompted (step 84) that data collection is complete and to send the test requests and collected data to server 50 for processing (step 86). The transfer is conducted using FTP or other suitable protocols over the internet or via another wired or wireless matter of communicating electronic data over distances that may be significant.

FIG. 1 illustrates the two-way communication of a plurality of DCUs 20 with processing server 50. Once test requests and data are sent to server 50, processing continues as discussed with reference to FIG. 4 below. When the tests are complete at server 50, the results are returned to the respective DCU. Processing logic within the DCU awaits return of the results (step 90) which are stored while the user is preferably prompted that the results are ready (step 91). The user is provided with onscreen selection or other means for selectively viewing the assessment results (step 92). The results are displayed and a user may receive then in any suitable manner, onscreen viewing, printout, saved electronic file, e-mailed, etc. (step 94).

Referring to FIG. 4, a flow diagram of processing in the assessment processing server in accordance with the present invention is shown. Communication from a DCU is identified and authenticated (step 102), then test request and the corresponding data are received (step 104, 106). A determination is made that the data type and amount conform to that required for the requested assessment (step 110). If not, a user or operator is informed so that the tests and data can be resent or troubleshooting steps initiated (step 108).

The requested tests are then performed. Each of the tests is discussed below in more detail with respect to FIGS. 5-14. A first level of processing or result analysis may be performed as discussed below (step 112) and these results are returned to the DCU that initiated the tests (step 114).

As illustrated in FIG. 1, system 10 may include an additional processing computer 70 that can provide additional processing power either running additional analyses or taking some of the processing demands off of server 50 so that that computer may more efficiently process and route test requests, data and results between the various DCUs. If an additional processing computer 70 is utilized, tests allocated for it are conducted (step 116) and the results may be returned to the user electronically or otherwise returned, eg. emailed, discussed in a consultation, etc. Processing flow then loops awaiting the next test request (step 118) from which flow returns to the authentication and receipt functions of steps 102-106.

A description of machine executable steps of the tests selectable in step 80 of FIG. 3 and performed in step 112 of FIG. 4 is now presented.

Heart Rate Variability (HRV) Test—Cardiac

The heart rate variability test (HRV) is designed to give an indication of the state of the biological systems that regulate cardiac activity. The cardiac system functions best when it is regulated by the autonomic circuit. When homeostasis is broken (unbalanced) higher levels of the central regulatory system dominate cardiac activity. These changes in regulation are reflected in the variability of the heart rhythm. Processing cardiac signals as discussed below permits quantitative and qualitative analysis of the functional state of cardiac activity.

The following is a representative HRV test. It should be recognized that HRV tests that differ from that taught below are within the present invention when similar or producing similar results or when provided with one or more of the other types of tests taught herein.

In general, an HRV test conducted via system 10 records sensor data, constructs charts or "grams" (i.e., scatter-grams, histograms, frequency spectrum-grams, etc.) that reflect the sensed data, calculates indices from the grams and data, and performs rules based analysis of the indices values to generate textual conclusions of the functional state of cardiac activity.

Figure 5:
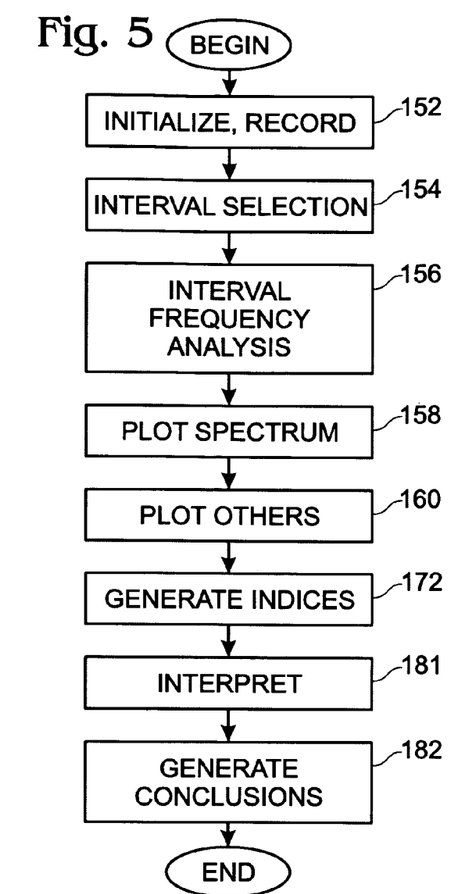
FIG. 5 is a flow diagram of machine executable steps for a representative HRV test in accordance with the present invention.
Figure 6:
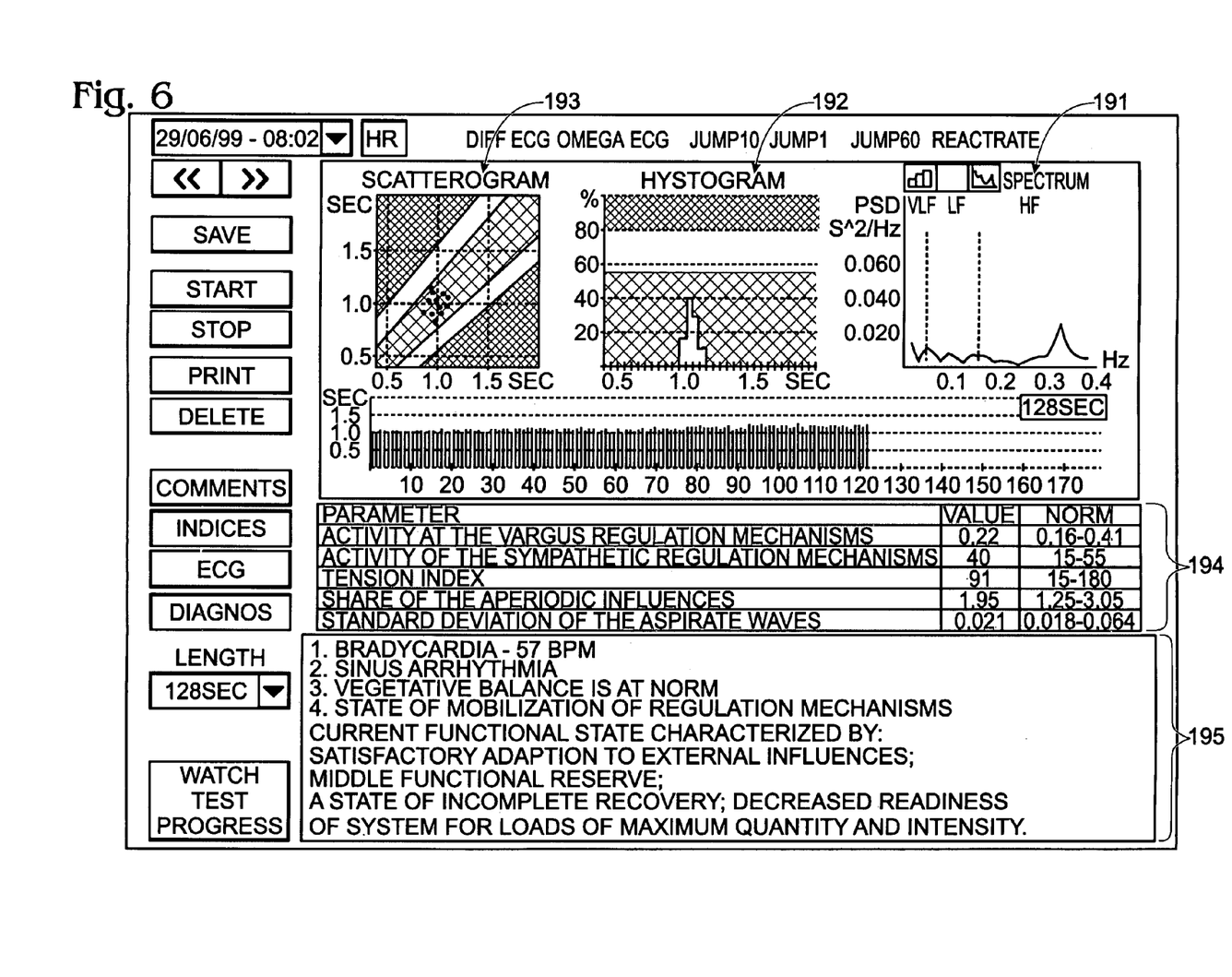
FIG. 6 illustrates a display of data generated in the HRV test of FIG. 5 in accordance with the present invention.

A representative HRV test is described with reference to FIG. 5, which illustrates a flow diagram of machine executing steps for a HRV test in accordance with the present invention. The steps of FIG. 5 and those of the other tests described herein are preferably achieved with application software executing on the processor of CD 50 or via execution of machine executable steps using other current or future developed technology. FIG. 6 illustrate a representative display of HRV test results that preferably includes a cardiogram, the above-mentioned charts/grams and textual conclusions of functional state.

In this representative HRV test, four electrode sensors are preferably utilized and they are preferably placed one each on the wrists and ankles. One sensor electrode is a ground and the other three collect standard ECG data or the like. Alternative sensor placement may be utilized. The HRV test is based on the registration of cardiac contractions of standard electrocardiogram (ECG) readings over the course of a fixed span of time. The test records the change of period length (in seconds) between each cardiac contraction which is the time between ECG spikes, which are designated with the letter R.

After initialization, cardiac muscle electrical activity is recorded for a fixed time period, e.g., 128 seconds (step 152). This data is sent to processing server 50. A fixed number of consecutive heart beat intervals (RR intervals), e.g., 100, is selected and analyzed (step 154). The intervals are processed in this preferred method using a fast fourrier transformation to achieve frequency spectrum analysis (step 156) and the density of interval frequencies is plotted in a frequency spectrum-gram 191 (step 158, see FIG. 6). Frequency spectrum analysis is known in the art. The following frequency ranges are preferably plotted: high frequency=0.15 to 0.4 Hz; low frequency=0.04 to 0.15 Hz; and very low frequency=0.004 to 0.04 Hz. A histogram 192 and a scattergram 193 are also preferably generated and displayed (step 160).

In steps 172, various preferred indices for cardio system performance are respectively calculated based on frequency spectrum and other data and these include:

Vagus (parasympathetic) Regulation (VR);
Humoral Regulation (HR);
Sympathetic Regulation (SR);
Stress Index;
Share of aperiodic influences;
Standard deviation; and
Frequency of Cardiac Contractions (FCC).

Calculation of these or related indices is known in the art. (See Baevskiy, R. M., et al., *Mathematical Analysis of Changes in Heart Rate Rhythm Under Stress*, Moscow Science, 1984).

These indices (194) are interpreted (step 181) to generate (step 182) textual conclusions about the functional state of cardiac activity. This is preferably done with a rules-based analysis discussed below. Condition statements are preferably generated for at least:

1. type of rhythm;
2. type of regulation of rhythm; and
3. type of vegetative homeostasis.

The type of rhythm is the heart beat rate. Type of regulation is based on VR (related to a norm) and conclusions may include sinus arrhythmia (which is normal), stable rhythm, pace-maker dysfunction, etc. Type of vegetative homeostasis is based on HR, VR, and SR and reflects an evaluation of the balance between parasympathetic and sympathetic regulation of the heart. The indices may also be used to generate other conclusions about the functional state of the cardiac system including degree of stress of the regulatory mechanism (from normal to state of dysfunction), reserve status (from high to very low), readiness of system for loads (from optional to severe cardiac dysfunction demanding immediate cardiology consultation) and adaptation to external influences (from stable to breakdown in adaptation). The results are returned to the data collection unit that initiated the test for display.

The textual conclusions are depicted with reference number 195 in FIG. 6.

Differential ECG (DECG) Test—Metabolism

The heart is a cardiac muscle and energy metabolism in the heart can be monitored with an ECG. Since there is a known correlation between energy metabolism in cardiac muscles and in skeletal muscles, conclusions about the state of skeletal muscles can be drawn from analysis of cardiac muscle energy metabolism.

Figure 7:
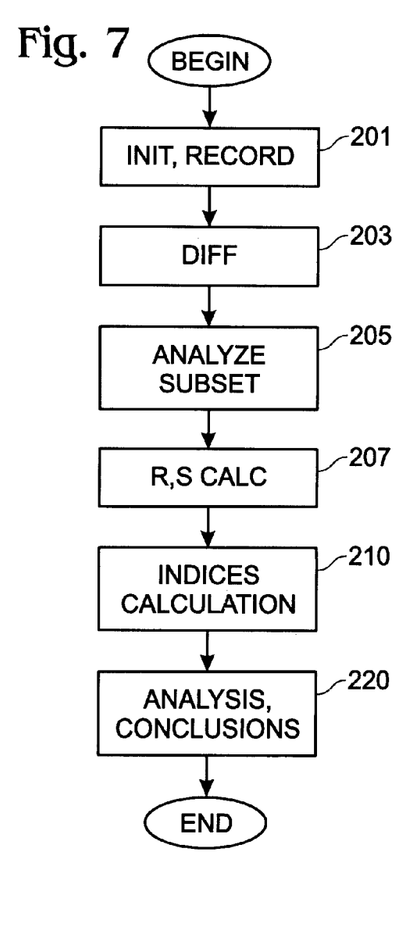
FIG. 7 is a flow diagram of machine executable steps for a representative differential ECG test in accordance with the present invention.
Figure 8:
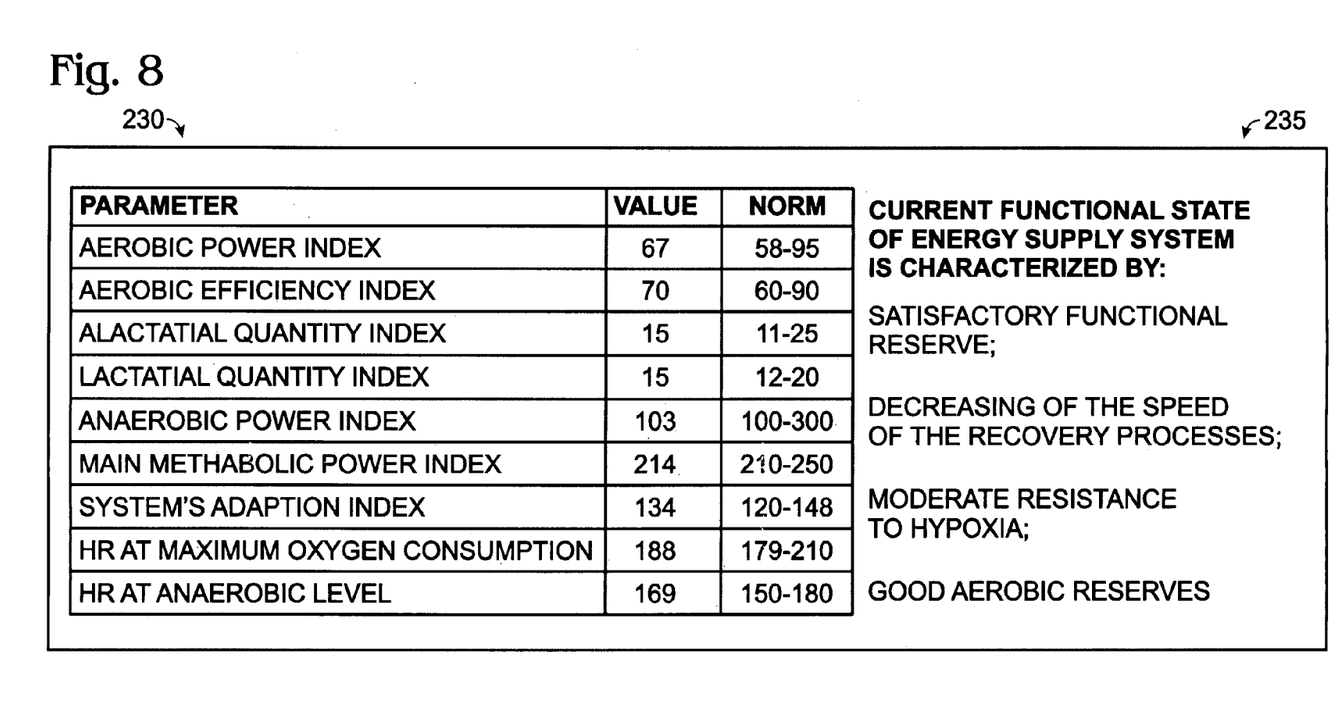
FIG. 8 illustrates a display of data generated in the DECG test of FIG. 7 in accordance with the present invention.

A representative DECG test is described with reference to of FIG. 7, which illustrates a flow diagram of a machine executing steps for a DECG test in accordance with the present invention. It should be recognized that various DECG tests may be utilized without departing from the present invention. FIG. 8 illustrates a representative display of DECG test results that preferably includes calculated indices and textual conclusions of the functional state of the metabolic system.

To perform a representative DECG test, seven electrode sensors 21-27 are preferably utilized. These include the four electrodes used in the HRV test 21-24 and three more electrodes 25-27 that are place on the chest in a standard ECG arrangement, though 26 is preferably placed on the right side of the chest.

In step 201, ID 40 is initialized and ECG data is recorded from each sensor for a predefined time period, e.g., 120 seconds. This data is sent to the processing server 50 for processing. The received ECG signals from the chest sensor electrodes are preferably differentiated (step 203) and analyzed (step 205). A subset, e.g., 10-60 (30 in the present example), of consecutive QRS complexes (peak and recovery of differentiated heart beat contraction) are analyzed and R and S values are ascertained (step 207).

In steps 210, indices for the representative DECG test are generated from the sensed data (preferably including averaged R and S values). These indices include the anaerobic power index (API) which is the magnitude of maximum oxygen consumption, VO2 max, the alactic capacity index (ALCI), the lactic capacity index (LCI), the anaerobic capacity index (ACI), the aerobic efficiency index (AEI), and the system adaptation index (SAI). Calculation of these or related indices is known in the art. (See publications of Kiev Sports Medicine University by Beregovog, V. Y., or Dushanin, S. A. (1986)).

These indices are then analyzed (step 220) to generate textual conclusions about the functional state of the metabolic system. This analysis is preferably carried out using a rules-based analysis as discussed below. The generated condition statements preferably address:

1. state of functional reserves;
2. speed of recovery process;
3. resistance to hypoxia (oxygen debt); and
4. aerobic reserves.

Each of these items may range from high to low and the generate textual conclusions preferably state the corresponding level. These results are propagated to the data collection unit that initiated the test for display or print out, etc.

The indices and textual conclusion are depicted in FIG. 8 with reference numerals 230 and 235, respectively.

Omega Wave (OW) Test—Circulatory, Detox, Hormonal, CN

Omega brain waves and omega brain wave potential (an electrical measurement of omega brain wave magnitude) have been shown to have a relationship to the performance of the central nervous, circulatory, detoxification and hormonal systems.

The following is a representative omega wave (OW) test. It should be recognized that tests that differ from that taught below are within the present invention when similar or producing similar results or when combined with one or more of the other tests taught herein.

Figure 9:
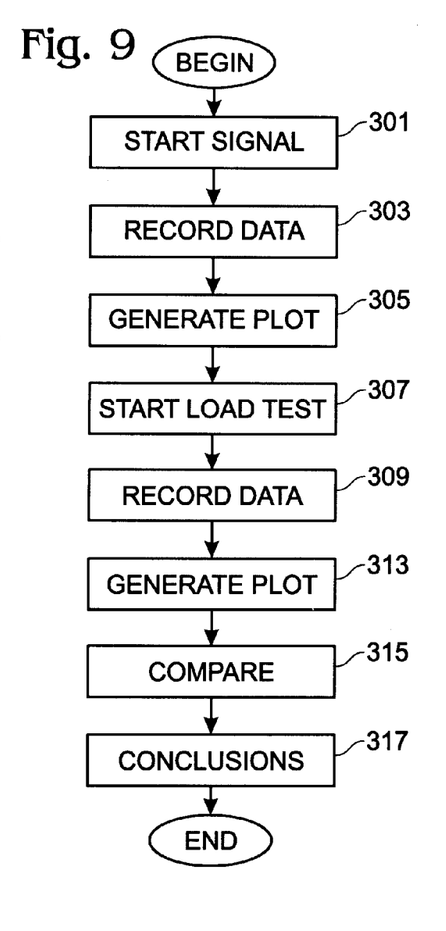
FIG. 9 is a flow diagram of machine executable steps for a representative omega brain wave test in accordance with the present invention.
Figure 10:
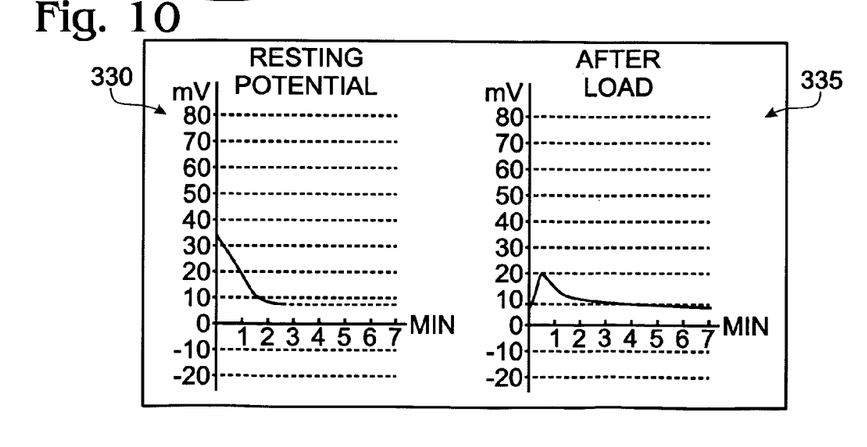
FIG. 10 is a display of data generated in the omega wave test of FIG. 9 in accordance with the present invention.
Figure 11:
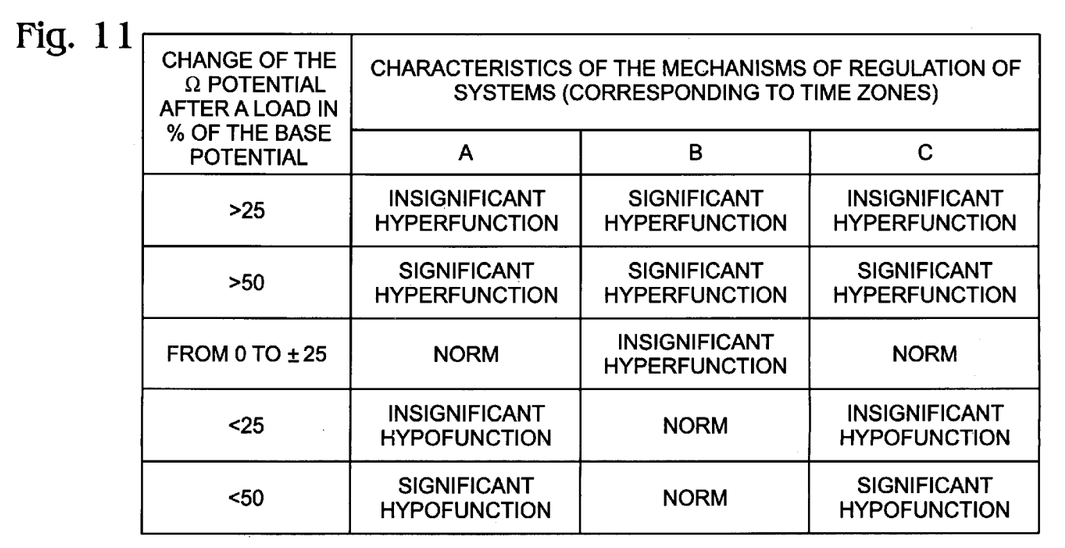
FIG. 11 is a diagram that illustrates an interpretation of differences between base and post-load omega potentials in accordance with the present invention.

A representative test is described with reference to FIG. 9, which illustrates a flow diagram of machine executable steps for a OW test in accordance with the present invention. FIG. 10 illustrate a display of OW test results that preferably includes charts of resting omega potential v. time, post-load omega potential v. time and textual conclusions of functional state. The textual conclusions discussed below and those shown in part in FIG. 11 are not shown in FIG. 10.

The base omega potential at rest has been identified as an indicator of the level of the functional state of the central nervous system and its adaptive reserves. Three levels of base omega potential have been empirically differentiated in healthy people and these are low level (<0 mV), medium level (0-40 mV), and high level (41-60 mV). Low level is characterized by a lowered level of wakefulness, quick exhaustion of psychic and physical functions, unstable adaptive reactions and limited adaptive potential. Medium level is characterized by an optimal level of wakefulness, high stability of psychic and physical functions, sufficient adaptive potential and stable adaptive reactions. High level is characterized by a state of psychic-emotional tension, high stability in response to loads and adequate adaptive reactions.

Iberal and McCullock have shown in their research that there is a time scale for turning on various system resources in response to a stress (i.e., post-load potential). Empirical data has shown that the dynamics of omega potential after an external stress are closely related to the dynamics of various body system processes being turned on. As a result, three time zones of omega potential change, after a single stress load, have been identified and they are Zone A (0-1.5 minutes), Zone B (1.5-4 minutes), and Zone C (4-7 minutes). Zone A characterizes the functional state of the cardio-respiratory (circulatory) system. Zone B characterizes the functional state of the detoxification system (i.e. gastro-intestinal tract, liver and kidneys, etc.). Zone C characterizes the functional state of the hypothalmic, hypophysial and adrenal glands (hormonal system).

The omega wave test is preferably conducted with chlorine-silver weak-isolating electrodes. The electrodes are placed on the test subject (one at the center of the test subject's forehead and one at the base of the right thumb) while the test subject is either sitting or lying in a state of rest.

In step 301, processing logic on CD 50 generates a test start signal and initiates receipt of sensed omega wave potential from ID 40. These signals are preferably recorded for a pre-defined time period (step 303), preferably approximately seven minutes, after which a test end signal is generated. This data is sent to processing server 50 for analysis and processing. Plot 330, generated in step 305, illustrates a representative plot of the data. The base potential provides a base line from which to access post-load potential.

To perform the post-load assessment, a start signal is generated by CD 50 (step 307) and the SUT undertakes a physical load such as one or two rapid knee bends. The omega potential of the SUT is recorded for a fixed period of time (step 309), approximately seven minutes, after which an end test signal is generated. A graphic representation of the results of the post-load test is preferably generated and plotted as plot 335 (step 313).

The base and post-load potentials are then compared (step 315) in each zone and textual conclusions (step 317) are generated based on the percent difference between the base and post-load potentials, consistent with the chart of FIG. 11. The textual conclusions are preferably generated with a rules-based analysis as discussed below.

In Zone A (circulation), the textual results preferably indicate a state ranging from significant hyperfunction to normal to significant hypofunction.

In Zone B (detoxification), the textual results preferably indicate a state ranging from normal function to markedly overloaded.

In Zone C (hormonal-adrenal), the textual results preferably indicate a state ranging from significant hyperfunction to normal to significant hypofunction.

With respect to the central nervous system (CNS), textual conclusions, based on the measured base omega potentials (discussed above) are also preferably generated. These include conclusions that address the state of adaptive reaction of the CNS (ranging from adequate to a restriction in the effectiveness and quality of the adaptation reaction), resistance of CNS to physical and psychic loads (ranging from satisfactory to low resistance) and level of activity of CNS (ranging from optimal to low). The test results are propagated to the appropriate DCU 20.

Jump Test—Neuro-Muscular

Figure 12:
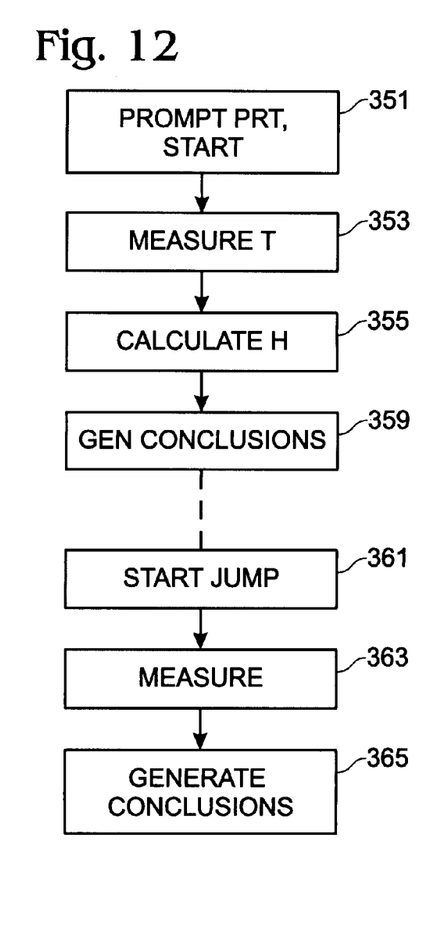
FIG. 12 is a flow diagram of machine executable steps for a representative jump test in accordance with the present invention.

Referring to FIG. 12, a flow diagram of machine executable steps for a representative jump test in accordance with the present invention is shown.

The following is a representative jump test. It should be recognized that tests that differ from that taught below are within the present invention when similar or producing similar results or when combined with one or more of the other tests taught herein.

The jump test preferably includes one or more of the several component jump tests. The component jump tests preferably include a single series, a ten second and sixty second jump test.

In the single series test, computer prompts a SUT to jump a fixed number of times, e.g. five (step 351). A jump is completed before a signal for the next jump is issued. Time of flight is measured via pad sensor 38 (step 353) to calculate jump height (step 355). Averaged values are preferably calculated. This test measures readiness for explosive efforts and generates appropriate textual conclusions (step 359) based on performance (from high readiness to low readiness).

The ten second jump test is designed to monitor speed and power potential in the alactic regime. Computer 30 generates a start signal (step 361) and a SUT jumps as high and as often as he or she can in ten seconds. Number of jumps, time in air, i.e. height, and time on contact surface (which represents rest or readjustment) are measured (step 363). These parameters are essentially indices and they are interpreted to generate the textual conclusions stated below.

The sixty second test is similar, but lasts for sixty seconds. It is designed to monitor speed and power potential in the lactic regime.

Textual conclusions for the ten second test include speed and power in the alactic regime (from high specific power to low specific power) and share of speed and power components (from dominance of speed to shared to dominance of power).

Textual conclusions for the sixty second test include speed and power potential in the lactic regime (from high specific power to low specific power) and speed-power endurance (from high to low).

The textual conclusions are preferably generated with a rules-based analysis of jump test data. They may be generated in processing server 50 and propagated to computer 30 for display or wholly within computer 30.

Stimulus Response (SR) Test—Central Nervous System (CN)

Figure 13:
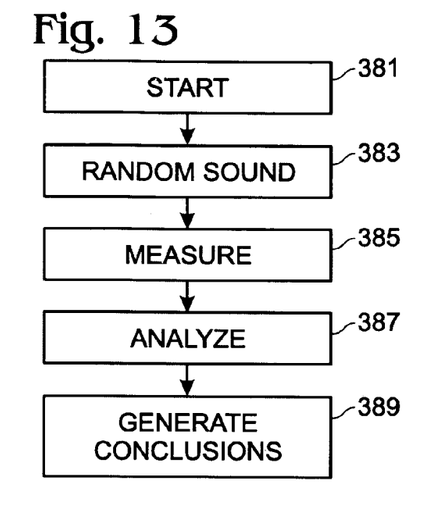
FIG. 13 is a flow diagram of machine executable steps for a representative stimulus response test in accordance with the present invention.

Referring to FIG. 13, a flow diagram of machine executable steps for a representative stimulus response test in accordance with the present invention is shown.

The following is a representative stimulus response test. It should be recognized that tests that differ from that taught below are within the present invention when similar or producing similar results or when combined with one or more of the other tests taught herein. It should also be recognized that while sound is used as the stimulus in the test below, other sensory signals may be used such as those based on light, visual cues, mechanical or tactile sensation, etc.

The SR test monitors the functional state of the central nervous system and, more specifically, reaction capabilities.

The test preferably consists of a series of sounds generated in a fixed time period to which a SUT has to respond.

Computer 30 generates a test start signal (step 381) and then randomly generates fifty sounds in a one minute period (step 383). The SUT presses button 39 (FIG. 1) in response to each sound. The delay in response is measured for each sound (step 385). This data is processed to determine the speed and consistency of response (step 387). Mistakes such as pressing the button too soon (anticipating the sound) or too late (loss of concentration) are also recorded.

These parameters or indices are then analyzed (389) to generate textual conclusions that preferably concern:
1. ability of the CN to respond;
2. stability of the neurological processes that determine reaction rate; and
3. reaction rate.

Each of these items is preferably indicated as ranging from high to low. The textual conclusions are preferably generated with a rules-based analysis of stimulus response data. They may be generated in processing server 50 and propagated to computer 30 for display or wholly within computer 30.

Rules-Based Analysis

Each of the above tests preferably incorporates a rules-based analysis to interpret indices, graphs and/or other sensed data and to then generate therefrom textual conclusions indicative of functional state of a SUT. The rules-based analysis preferably includes at least a first part and a second part, which are shown diagrammatically in FIG. 14.

Figure 14:
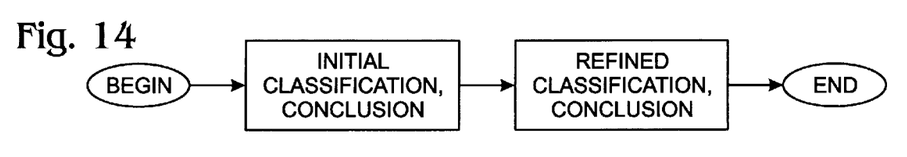
FIG. 14 is a flow diagram of rules-based analysis in accordance with the present invention.

In a first part (step 401), the values of relevant indices, parameters or omega potential differences, etc. (depending on the test), are examined and classified for each desired conclusion category or type, e.g., state of functional reserves, in the DECG test. The classification may be based on where a value lies in a range of values calculated from a wider population, or relative to another parameter/index detected during a test (e.g., parasympathetic and sympathetic indices, or base and post-load omega potentials, etc.), or based on an absolute value or compared to some other appropriate standard, etc. The classification may also be dependent on the interaction of multiple indices and/or other information.

In a second part (step 405), the initial classification is re-analyzed and refined, if necessary, e.g., if it falls within a certain distance of another classification or if there is conflicting information, etc. This refinement may include looking at another parameter/indices when a value is near the border between two different classifications' or reclassifying a value due to a significant deviant value of another related parameter/index, or to compensate for an outlier, etc. A change in classification based on refinement will likely lead to a change in textual conclusion. Various rules-based algorithms are known in the art and these could be modified by a skilled practitioner to implement the criteria set forth above for the listed tests.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features herein before set forth, and as fall within the scope of the invention and the limits of the appended claims.

The invention claimed is:

1. An apparatus for assessing the functional state of a subject under test, comprising:
    a plurality of data collection units each including a user interface and a processing logic, the data collection processing logic permitting a user to request one or more functional state test from the group of test including:
    heart rate variability test,
    differential ECG test,
    brain wave test,
    jump test, and
    stimulus response test;
    a processing server configured for location at a distance from each of the data collection units and couplable through a network connection to the data collection units;
    wherein the processing server includes processing logic that receives test requests and corresponding collected data from a data collection unit and performs the one or more requested functional state tests to produce a signal for that given test that is representative of a textual conclusion of the functional state of a body system that that test is designed to assess.

2. The apparatus of claim 1, wherein a data collection unit is configured to receive the representative signal for a test that that unit initiated from the processing server via the network connection and to present that representative signal, in response to input through the user interface, in a manner that is readable to a user.

3. The apparatus of claim 1, further comprising a supplemental processing computer electronically couplable to the processing server that performs additional analysis of one or more of the functional state tests.

4. The apparatus of claim 1, wherein the network is the internet.

5. The apparatus of claim 1, wherein the network includes a wireless link.

6. The apparatus of claim 1, wherein the server processing logic performs two or more of the functional state tests.

7. The apparatus of claim 1, wherein the server processing logic performs the brain wave test and that test includes analysis of omega brain waves.

8. The apparatus of claim 1, wherein the signal representative of the textual conclusion is generated from a rules-based analysis of sensed data as processed by the processing logic.

9. The apparatus of claim 1, wherein said processing logic is configured to calculate one or more indices values for the given test and to interpret said one or more indices values to general said signal representative of said textual conclusion.

10. The apparatus of claim 1, further comprising a mechanism that non-invasively measures physical parameters of a subject under test that correspond to the one or more functional state tests.

11. A method of assessing the functional state of a subject under test, comprising the steps:
    receiving at a data collection unit located at a first physical location one or more functional state test requests from the group of physical state tests including:
    heart rate variability test,
    differential ECG test,
    brain wave test,
    jump test, and
    stimulus response test;

propagating from the data collection unit via a network connection the received one or more test requests and corresponding collected data to a processing computer located at a second physical location, spaced from the first location;

conducting at the processing computer the one or more requested functional state tests and generating a test results signal for each conducted test;

propagating from the processing computer to the data collection unit the test result signal for each conducted test; and presenting the test results in a readable manner to a user at the data collection unit.

12. The method of claim 11, wherein the step of propagating from the data collection unit via a network connection includes the step of propagating from the data collection unit via a wireless network connection.

13. The method of claim 11, wherein the step of conducting one or more requested functional state tests includes the step of conducting at least two requested functional state tests.

14. The method of claim 11, wherein the test conducting step includes the step of conducting the brain wave test with analysis of omega brain waves.

15. The method of claim 11, wherein the test conducting step includes the step of performing a rules-based analysis of sensed data.

16. The method of claim 11, wherein the test conducting step includes the steps of calculating one or more indices values for a given test and interpreting the one or more indices values to general the test result signal.

17. The method of claim 11, wherein the receiving step includes the step of non-invasively measuring physical parameters of a subject under test that correspond to one or more of the functional state tests.

* * * * *